(12) United States Patent
Holt et al.

(10) Patent No.: US 10,034,605 B2
(45) Date of Patent: Jul. 31, 2018

(54) SYSTEMS, METHODS, AND DEVICES FOR DETECTION AND DIAGNOSIS OF BRAIN TRAUMA, MENTAL IMPAIRMENT, OR PHYSICAL DISABILITY

(71) Applicants: Jonathan T. Holt, Merritt Island, FL (US); Kurtis W. Sluss, Whitestown, IN (US); Heya Kaakeh, West Lafayette, IN (US); James Waggoner, Carmel, IN (US); Michael Heims, Indianapolis, IN (US); Craig Wilhite, Newburgh, IN (US)

(72) Inventors: Jonathan T. Holt, Merritt Island, FL (US); Kurtis W. Sluss, Whitestown, IN (US); Heya Kaakeh, West Lafayette, IN (US); James Waggoner, Carmel, IN (US); Michael Heims, Indianapolis, IN (US); Craig Wilhite, Newburgh, IN (US)

( * ) Notice: Subject to any disclaimer, the term of this patent is extended or adjusted under 35 U.S.C. 154(b) by 0 days.

(21) Appl. No.: 15/456,139

(22) Filed: Mar. 10, 2017

(65) Prior Publication Data
US 2017/0311799 A1    Nov. 2, 2017

Related U.S. Application Data

(60) Provisional application No. 62/329,837, filed on Apr. 29, 2016.

(51) Int. Cl.
| | | |
|---|---|---|
| *A61B 3/14* | (2006.01) | |
| *A61B 3/11* | (2006.01) | |
| *A61B 5/00* | (2006.01) | |
| *A61B 3/15* | (2006.01) | |
| *A61B 3/00* | (2006.01) | |

(52) U.S. Cl.
CPC ............ *A61B 3/112* (2013.01); *A61B 3/0025* (2013.01); *A61B 3/0033* (2013.01); *A61B 3/152* (2013.01); *A61B 5/4064* (2013.01)

(58) Field of Classification Search
USPC ................................................ 351/200–246
See application file for complete search history.

(56) References Cited

U.S. PATENT DOCUMENTS

| | | |
|---|---|---|
| 9,888,845 B2 | 2/2018 | Visconti |
| 2008/0253622 A1 | 10/2008 | Tosa et al. |
| 2012/0268715 A1 | 10/2012 | Stark et al. |
| 2015/0116665 A1 | 4/2015 | Finkel |

(Continued)

FOREIGN PATENT DOCUMENTS

WO    2015063598 A1    5/2015

OTHER PUBLICATIONS

Angel N. Boez, et al., Quantitative Pupillometry: Normative Data in Healthy Pediatric Volunteers, 103 J Neruosurg. (6 Suppl) 496-500 (2005).

(Continued)

*Primary Examiner* — Mohammed Hasan
(74) *Attorney, Agent, or Firm* — Indiana University Maurer School of Law IP Legal Clinic

(57) ABSTRACT

Systems, devices, and methods are disclosed which may be used to detect and determine the extent of brain trauma, mental impairment, physical disability, or other brain dysfunction by tracking one or more ocular responses.

11 Claims, 9 Drawing Sheets

(56) References Cited

U.S. PATENT DOCUMENTS

2015/0245766 A1\* 9/2015 Rennaker ............... A61B 3/112
                                                        351/210
2016/0192837 A1\* 7/2016 Neice ..................... A61B 3/112
                                                        351/206

OTHER PUBLICATIONS

Jose E Capo-Aponte et al., Pupillary Light Reflex as an Objective Biomarker for Early Identification of Blast-Induced mTBI, 2013 J Spine S4, available at www.readcube.com/articles/10.4172/2165-7939.s4-004.
William R. Taylor et al., Quantitative Pupillometry, a New Technology: Normative Data and Preliminary Observations in Patients with Acute Head Injury, 98 J Neurosurg. 205-213 (2003).
Mechal Ciesla, Przemyslaw Koziol, Eye Pupil Location Using Webcam, available at https://arxiv.org/ftp/arxiv/papers/1202/1202.6517.pdf.
Cihan Topal, Cuneyt Akinlar, An Adaptive Algorithm for Precise Pupil Boundary Detection Using the Entropy of Contour Gradients, available at https://ceng.anadolu.edu.tr/cv/eyetracking/download/PupilDetection.pdf.
Blaine R. Copenheaver, PCT Notification of Transmittal of the international Search Report and the Written Opinion of the international Searching Authority, or the Declaration, international search report and written opinion, dated Jul. 13, 2017, Alexandria, VA, USA.

\* cited by examiner

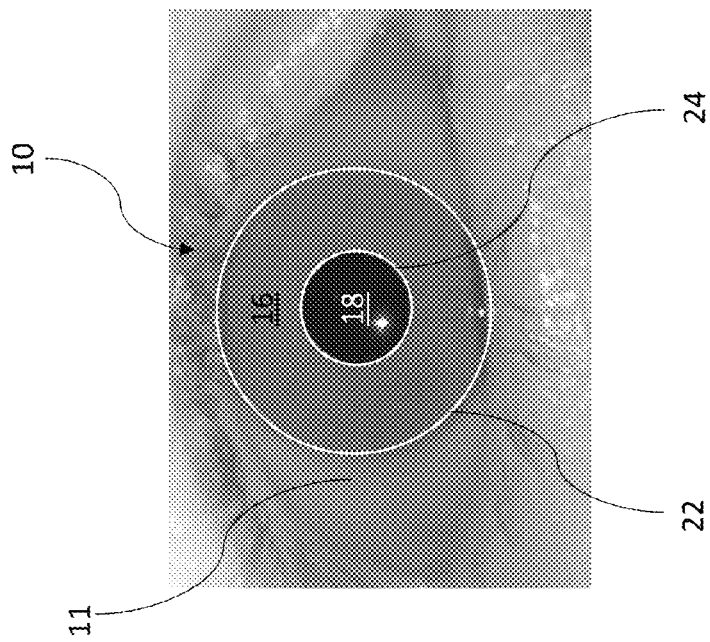
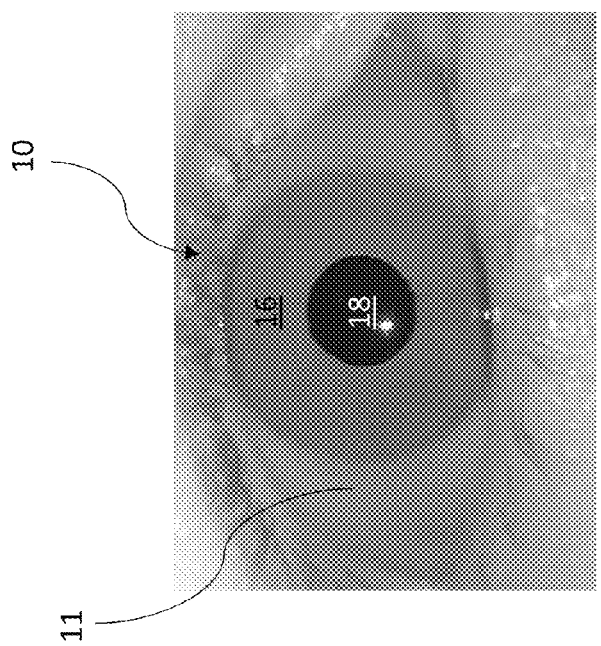
FIG. 3B
FIG. 3A

SYSTEMS, METHODS, AND DEVICES FOR DETECTION AND DIAGNOSIS OF BRAIN TRAUMA, MENTAL IMPAIRMENT, OR PHYSICAL DISABILITY

RELATED APPLICATIONS

The present application claims the benefit of U.S. Provisional Application No. 62/329,837, titled "Systems, Methods, and Devices for Detection and Diagnosis of Brain Trauma, Mental Impairment, or Physical Disability", to Holt et al., filed Apr. 29, 2016, the entire disclosure of which is incorporated by reference herein.

TECHNICAL FIELD

The present application relates to devices, systems, and methods for pupillometry and/or detecting brain trauma.

BACKGROUND

Brain trauma may occur when an external force causes brain dysfunction, usually by a violent blow or jolt to the head. According to recent reports from the CDC, 5.3 million Americans suffer from brain-related trauma each year. Inadequate resources to recognize and treat such trauma increase the scope of some of these injuries and their damage to the brain. In addition to brain trauma events, other conditions such as intoxication from alcohol or other substances and other brain disorders such as autism may be benefit from early detection.

An individual's neurological presence and condition is often evaluated through a subjective physical exam after symptoms have begun to present themselves. Some methods for detecting brain trauma that are currently available rely on qualitative tests, such as a series of questions or behavioral observations which may include substantial error, and may fail to assess the severity of the trauma or impairment. Other methods may rely on expensive or complex equipment which may not be available to general consumers, and may require substantial training and experience to use properly. Some methods require the patient to find a medical professional, or go to a hospital, which can take time. Prolonged recognition can increase the impact of trauma to the brain and offer opportunity to second impact syndrome.

SUMMARY

The present disclosure generally relates to systems, methods, and devices for pupillometry, and detecting and assessing brain trauma, mental impairment, or physical disability. In some aspects, the present disclosure includes methods for detecting brain trauma by tracking a pupillary response.

In one embodiment, a method for detection of brain trauma comprises providing a light stimulus to an individual's eye and tracking an optical response of the individual's eye. More specifically, in one embodiment, a method for determining risk of brain trauma, includes employing a pupillometry device which includes: a digital camera, a light element, a user interface, a computer processor, and computer memory. A user or patient orients a patient's eye to receive ambient light, and orients the digital camera to view the patient's pupil. The pupillometry device then emits a flash of light to the patient's pupil, captures a series of images of the patient's pupil, and determines the location and relative size of the patient's pupil in each image. The pupillometry device then determines, from the series of images and the relative size of the patient's pupil in each image, one or more rates of change of the size of the patient's pupil, and compares the rates of change of the size of the patient's pupil to one or more baseline rates of change to determine a risk level of brain trauma to the patient based on the deviation of the rates of change of the size of the patient's pupil from the one or more baseline rates of change. The device then indicates the risk level of brain trauma.

In another aspect, the present disclosure includes brain trauma detection devices. In one embodiment, a brain trauma detection device includes a camera, a lighting element, a computer processor, computer memory, and a display. In some embodiments, the brain trauma detection device may comprise a smartphone which includes a software application, such as an "app" which facilitates the detection of brain trauma by the use of one or more peripheral elements of the smartphone, such as a digital camera and a flash.

BRIEF DESCRIPTION OF THE DRAWINGS

The foregoing aspects of this disclosure will become more readily appreciated as the same becomes better understood by reference to the following detailed description when taken in conjunction with the accompanying drawings.

FIGS. 3A and 3B are photographs of a patient's eye taken with a brain trauma detection device showing superimposed feature boundaries in FIG. 3B.

Figure 1B:
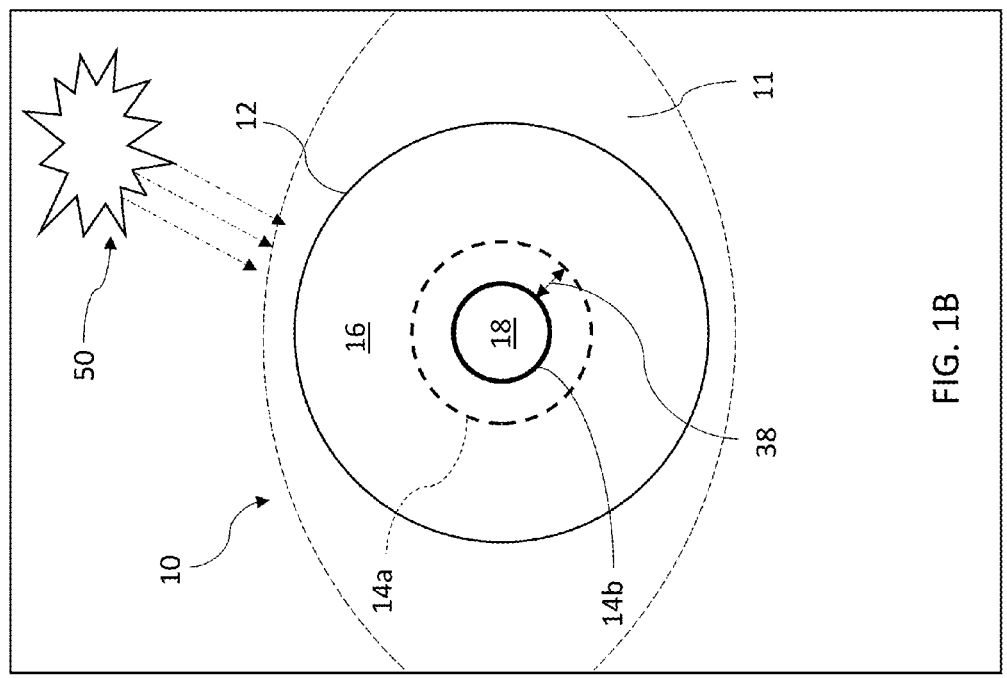
FIGS. 1A and 1B are before and after diagrammatic views of the effect of a light stimulus on a patient's pupil.

Corresponding reference characters indicate corresponding parts throughout the several views. The drawings represent embodiments of various features and components according to the present disclosure and, unless otherwise indicated, show the components in proportion to one another. The exemplifications set out herein are not to be construed as limiting the scope of the disclosure in any manner.

DETAILED DESCRIPTION

Brain trauma events occur in various settings, and may occur outside the presence of medical personnel and traditional medical equipment. For example, some brain trauma events may occur during recreational activities, such as sporting events, in which no medical personnel and/or traditional medical equipment are available to determine or diagnose the existence or extent of a head or brain injury, such as a concussion.

One indication of brain trauma or impairment can be observed with reference to a patient's eyes. In the absence of brain trauma or impairment, a patient's pupil can dilate or constrict at predictable constriction or dilation rates and modes in response to an amount of light incident on the pupil. The response of an unimpaired patient's pupil may be referred to as a "normal" response. The constriction rates and dilation rates for unimpaired patients may be substantially consistent for a particular group of patients. By contrast, when a patient suffers brain trauma, the patient's pupil may not constrict or dilate at predictable constriction or dilation rates and modes in response to an amount of light incident on the pupil, or may constrict or dilate in abnormal modes or rates. After a brain trauma event, one can detect the occurrence and/or risk of brain trauma by comparing the patient's pupil response to a normal response of an unimpaired pupil to determine whether the patient's pupil response was abnormal.

Figures 4A, 4B:
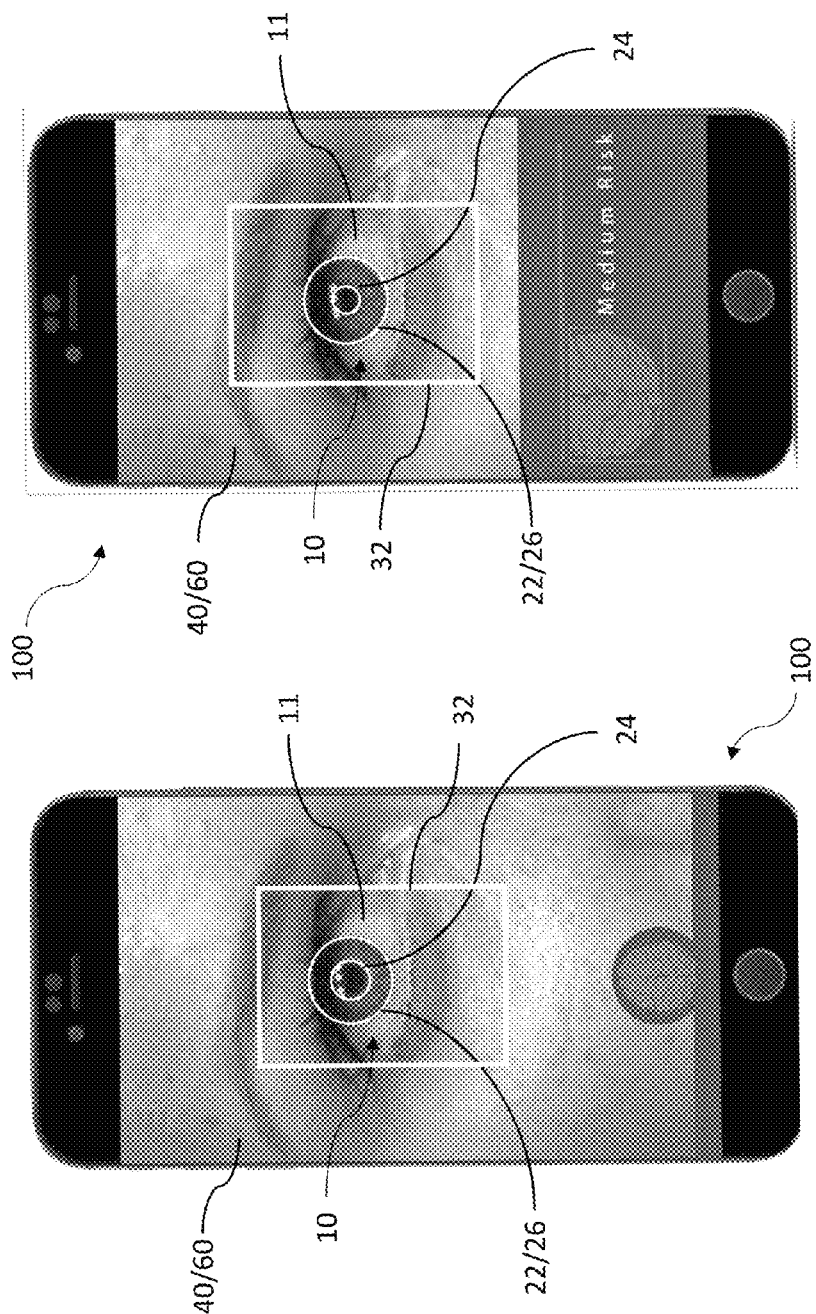
FIGS. 4A and 4B are side views of a brain trauma detection device, according to one embodiment, showing the brain trauma detection device displaying an image of a patient's eye with superimposed feature boundaries, and a brain trauma risk assessment in FIG. 4B.
Figure 5:
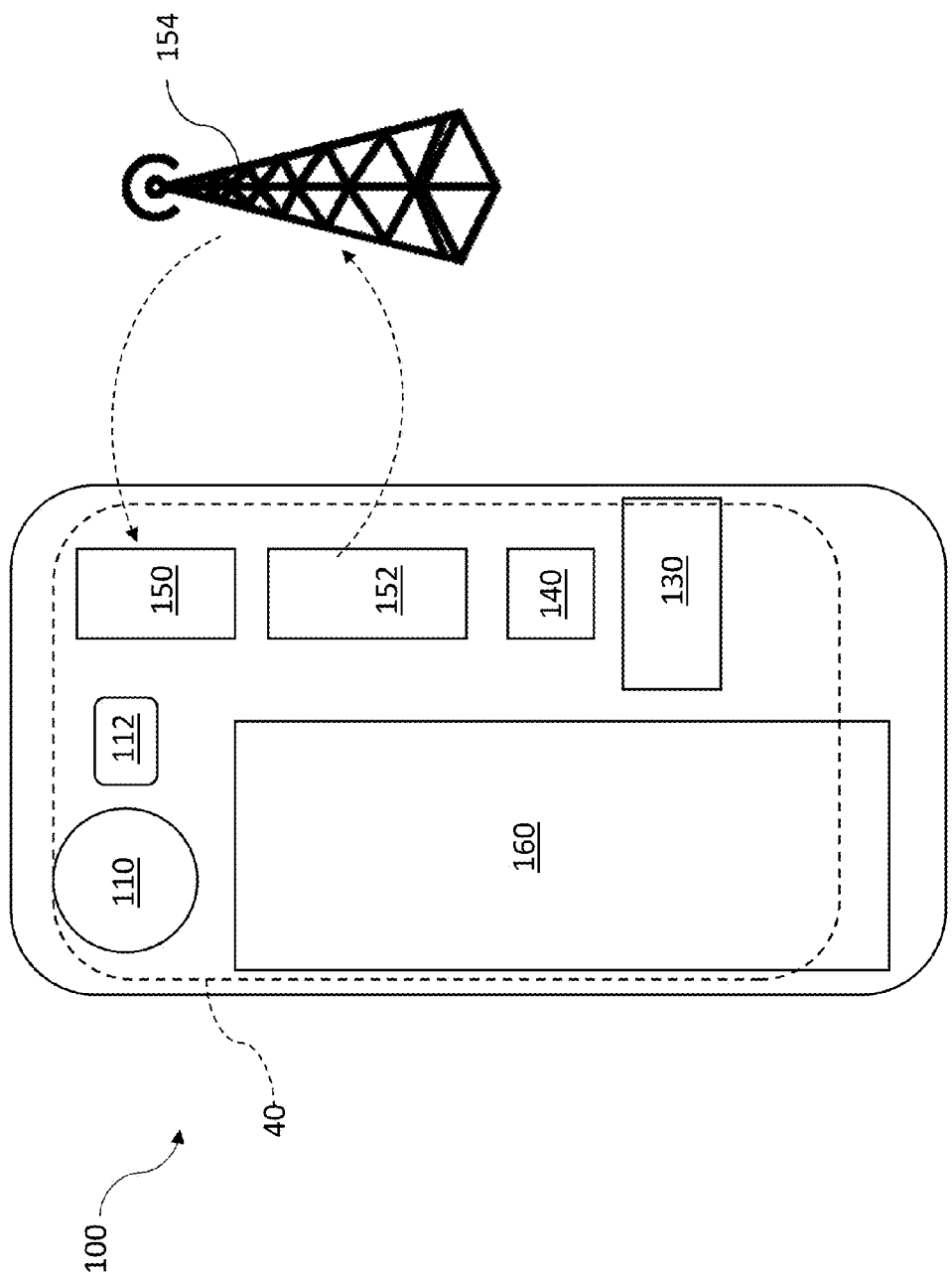
FIG. 5 is a diagrammatic view of a plurality of components of a brain trauma detection device, according to one embodiment.

The present application discloses a method for detecting brain trauma, which may include use of a brain trauma detection device 100, such as a smartphone. FIGS. 1A-3 illustrate a patient's ocular response to a flash of light 50. FIGS. 4a-5 illustrate a brain trauma detection device 100 configured to measure the patient's ocular response. FIGS. 6-9 illustrate a method for detecting brain trauma with brain trauma detection device 100.

In some embodiments, a method for detecting brain trauma may comprise the steps of positioning digital camera 110 (see FIGS. 5 and 6) to view and capture an image of a patient's eye 10, directing light at patient's eye 10 (see FIGS. 6 and 1B), capturing a plurality of images of eye 10 with camera 110 during, or after the light has been directed to eye 10, measuring one or more optical responses of eye 10, such as pupil constriction (see FIGS. 1B and 4B), and comparing the one or more measured optical responses to a reference point physiologic optical response.

Figure 1A:
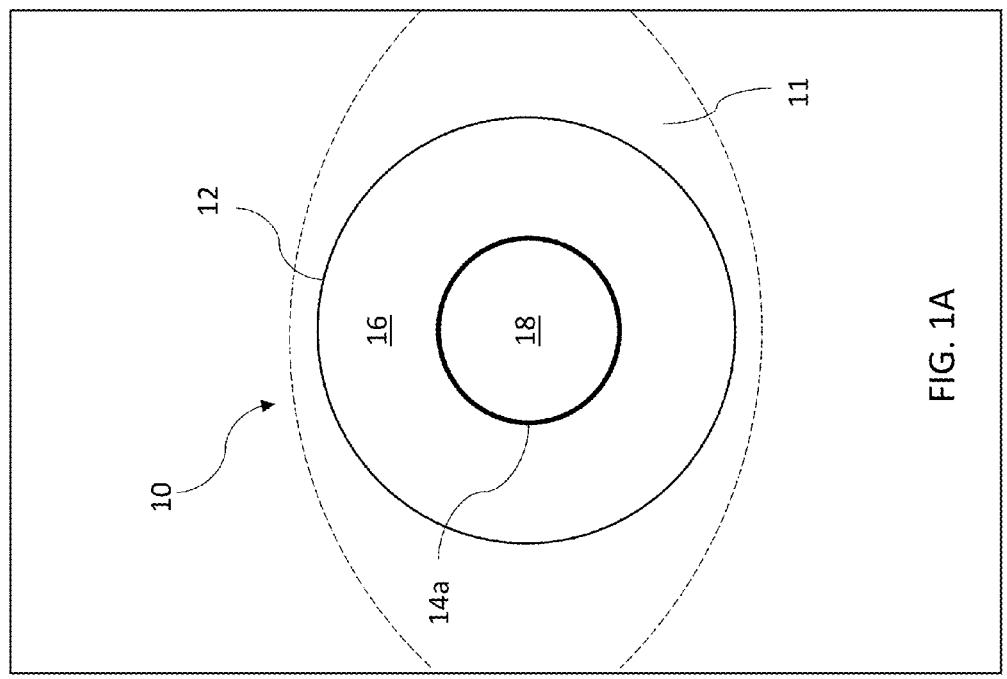

FIGS. 1A-1B are diagrammatic views illustrating the effect of light stimulus 50 on patient's eye 10. Light stimulus 50 may be a flash of light. Eye 10 includes pupil 18 and iris 16. Iris 16 is located within iris boundary 12. FIG. 1A illustrates eye 10 before stimulus 50 is applied to eye 10 and FIG. 1B illustrates eye 10 after stimulus 50 is applied to eye 10. Referring to FIG. 1A, pupil 18 is substantially concentric with iris 16, and is defined by or located within pre-stimulus pupil boundary 14a.

Referring to FIG. 1B, light stimulus 50 is applied to eye 10 by, for example, activating flash 112 on smartphone 100. As stimulus 50 impinges on patient's eye 10, pupil 18 normally constricts to limit or reduce the amount of light that passes through pupil 18. Pupil 18 constricts from pre-stimulus pupil boundary 14a to post-stimulus pupil boundary 14b by constriction radius 38. During constriction, pupil 18 passes through multiple stages of constriction at one or more constriction rates. A constriction rate may refer to the change in the diameter, radius, area, etc. of pupil 18 over time. The stages of constriction are recorded, observed, or photographed with camera 110 of brain trauma detection device 100 by repeated capturing and/or recording images of eye 10 during and after constriction until the eye's response stabilizes.

Figure 2:
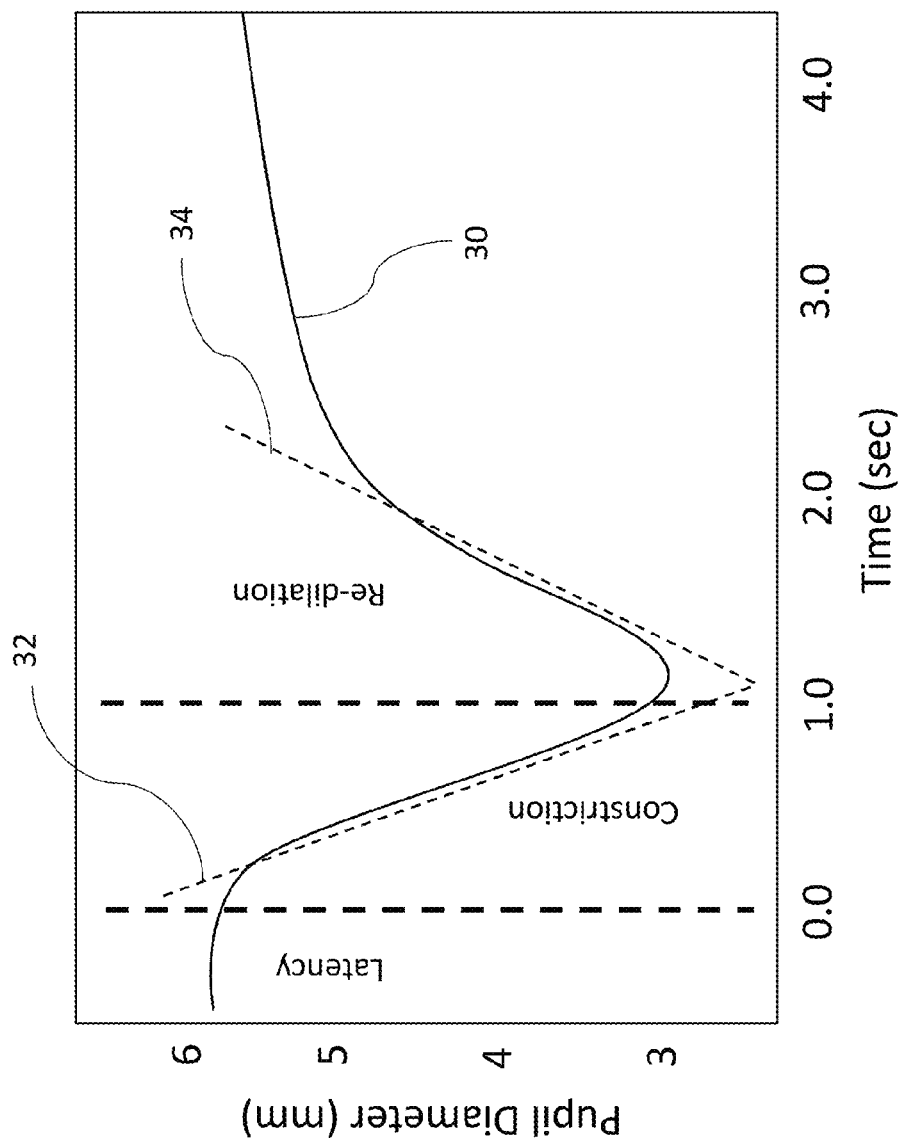
FIG. 2 is a graph illustrating the effect of a light stimulus on a patient's pupil.

FIG. 2 is a graph illustrating pupil response 30 of pupil 18 which is stimulated by a flash of light. Various stages of pupil response 30 are demarcated. In "latency" stage, pupil response 30 may be somewhat delayed. In "constriction" stage, pupil response 30 accelerates to constrict the size or diameter of pupil 18 to limit the amount of light that can pass through pupil 18. In constriction stage, pupil 18 constricts at constriction rate 32. In "re-dilation" stage, the flash of light has dissipated or ceased. Pupil 18 dilates to compensate for the change in light, and returns to substantially the same size as before the flash of light. In re-dilation stage, pupil 18 dilates at dilation rate 34.

FIGS. 3A-3B are photographs of an eye taken by brain trauma detection device 100 (see, e.g., FIGS. 4A-5). Brain trauma detection device 100 may also be referred to as a pupillometry device. According to one embodiment, brain trauma detection device 100 includes imaging analysis software configured to determine and/or measure one or more elements of image 60, such as iris 16 and pupil 18. Details regarding one embodiment of imaging analysis software are discussed below in connection with FIGS. 7-10. In FIG. 3A, the software demarcates pupil 18 by a region of relatively darker pixels when compared to the pixels of iris 16. Referring to FIG. 3B, imaging analysis software of brain trauma detection device 100 locates and demarcates pupil boundary 24 with reference to the region of relatively darker pixels when compared to an eye's iris 16. As pupil 18 constricts and dilates, the imaging analysis software measures differences in the size of pupil 18 between successive images. Because the elapsed time between each image can be known or fixed, the imaging analysis software can determine a rate at which the size of pupil 18 changes (i.e., dilates, constricts and/or redilates or expands) over time.

As shown in FIGS. 4A-6, a brain trauma detection device 100 is disclosed which may address one or more of the issues described above. In some embodiments, brain trauma detection device 100 includes a digital camera 110, a lighting element 112, such as a flash, a computer processor 140, digital memory 130, a power source 160, such as a battery, a receiver 150, a transmitter 152, and a screen 40. In some embodiments, brain trauma detection device 100 may comprise a smartphone, a tablet, or personal computing device.

Referring to FIGS. 4A-5, brain trauma detection device 100 may be a smartphone, which normally includes receiver 150, transmitter 152, computer processor 140, computer memory 130, digital camera 110, lighting element 112, such as a flash, battery 160, and screen 40. Brain trauma detection device 100 also includes a software package to facilitate a method for detecting brain trauma. Brain trauma detection device 100 functions by capturing images with digital camera 110, which is stored in digital memory 130. Computer processor 140 can analyze one or more features of image 60 and compare the one or more features in a first image (e.g., FIG. 4A) to the one or more features in a second image (e.g., FIG. 4B). In some embodiments, brain trauma detection device 100 sends data with transmitter 152, and receives data with receiver 150 from, for example, wireless communication hub 154 or another wireless communication device.

As pictured on screen 40 in FIGS. 4A and 4B, brain trauma detection device 100 provides image 60 of patient's eye 10 from digital camera 110 and locates and demarcates iris boundary 22 and pupil boundary 24. In one embodiment, brain trauma detection device 100 provides iris circle 26 of a pre-determined size on screen 40 to enable user 4 to align iris circle 26 with iris boundary 22 before lighting element 112 is activated. In other embodiments, brain trauma detection device 100 provides iris circle 26 on screen 40 automatically to match the location and size of iris boundary 22. Pupil boundary 24 may also be provided automatically by analysis of image 60 of eye 10 to locate certain points of interest of image, such as pupil 18. Screen 40 may also be referred to as a "graphical user interface" and may include touch screen features to allow a user to interact with device 100 running pupil measurement software.

Figure 6:
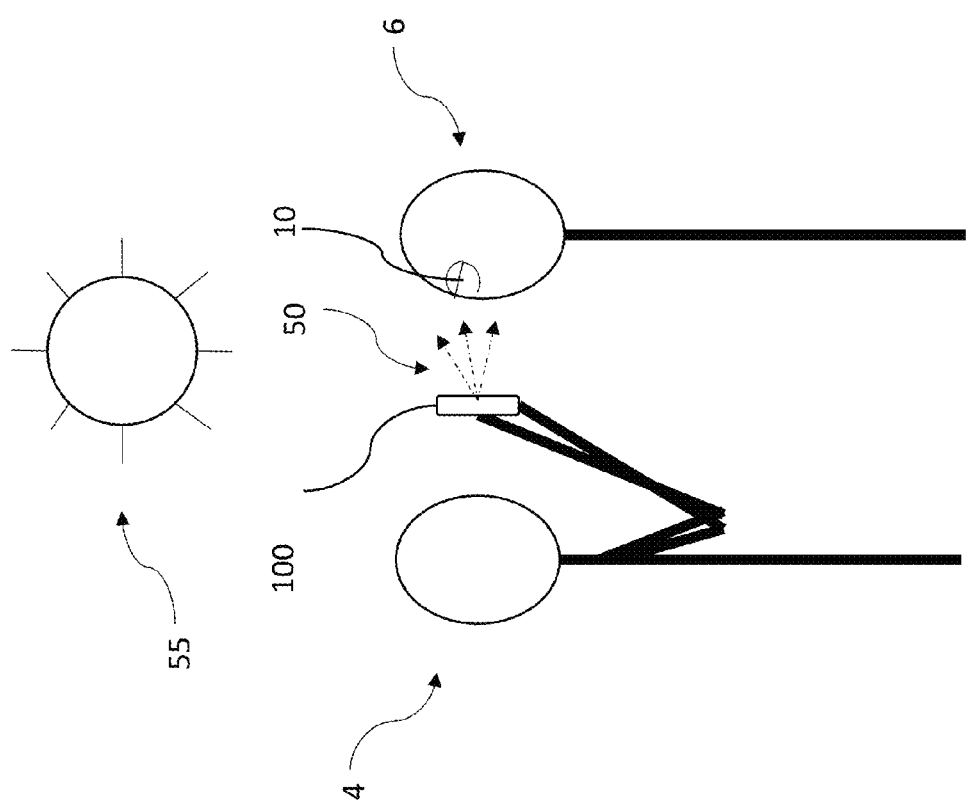
FIG. 6 is a side view of a user using a brain trauma detection device in an ambient light setting to detect potential brain trauma in a patient.

Referring to FIG. 6, user 4, uses brain trauma detection device 100 to detect brain trauma of a patient 6. User 4 directs digital camera 110 of brain trauma detection device 100 to take or capture an image of patient's eye 10. Brain trauma detection device 100 provides light stimulus 50 with flash 112 while capturing one or more images of patient's eye 10 with digital camera 110. Brain trauma detection device 100 can be used in a variety of settings, including outdoors and with ambient light 55, such as the sun or artificial lighting inside a building.

In one embodiment, brain trauma detection device 100 is used to detect, and/or determine the extent of, brain trauma, such as a concussion. As discussed earlier, brain trauma detection device 100 may be a smartphone or personal computing device equipped with brain trauma detection software, such as an "app," for imaging analysis and tracking. After patient 6 experiences a potential brain trauma event, user 4 may evaluate patient's condition by positioning digital camera 110 of brain trauma detection device 100 to photograph patient's eye 10. Brain trauma detection device 100 may take a plurality of successive images of patient's eye 10. Brain trauma detection device 10 also provides light stimulus 50, such as a flash, to direct light into patient's eye 10 to illicit a pupil response, such as pupil constriction or dilation. Brain trauma detection device 100 takes a plurality of successive images of patient's eye 10 during the pupil response.

As described earlier, the brain trauma detection software may be configured to determine and/or measure one or more elements in an image, such as pupil 18 and/or iris 16. The brain trauma detection software may determine the size of pupil 18 in each image, and may determine the rate at which the size of pupil 18 changes between successive images and over time. Brain trauma detection device 100 then compares the pupil response to one or more databases or model rates of change to determine whether the optical response is regular (i.e., indicates zero or negligible brain trauma) or abnormal (i.e., indicates significant brain trauma) or partially abnormal (i.e., indicates some brain trauma).

There may be a known "normal" baseline rate of constriction and/or dilation for a patient with no impairment or brain trauma (as discussed in the below attached article entitled *Pupillary Light Reflex as an Objective Biomarker for Early Identification of Blast-Induced mTBI*) and a known rate of constriction and/or dilation for a patient with high risk of impairment brain trauma. After comparing the optical response of patient's eye 10 against the databases or models, and after brain trauma detection device 100 calculates or determines the regularity or abnormality of the optical response, brain trauma detection device 100 indicates to user 4 and/or patient 6 whether, and to what extent, patient 6 has suffered brain trauma. For example, brain trauma detection device 100 may determine that patient 6 has a high, low, or medium risk. High risk may be determined or diagnosed where patient's pupil response is at or beyond the known abnormal rate of constriction and/or dilation, and medium risk may be determined or diagnosed where patient's' pupil response is between the normal and abnormal rates of constriction and/or dilation.

Figure 7:
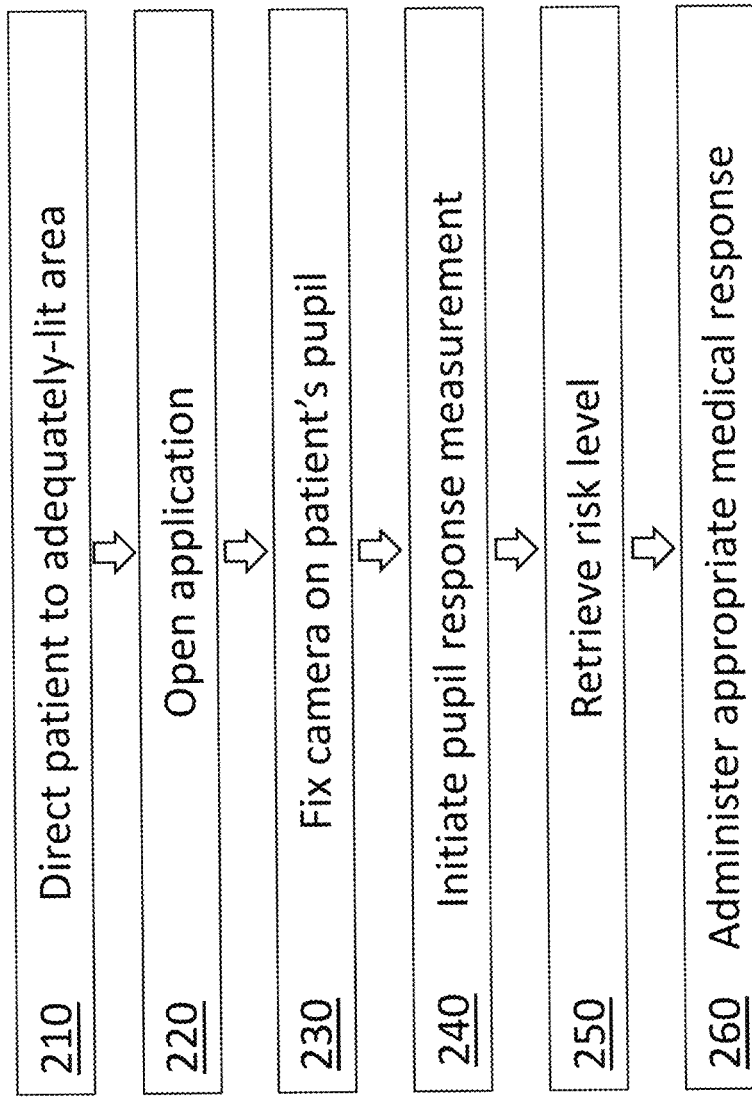
FIG. 7 is a flow chart diagram illustrating one embodiment of a brain trauma detection process.
Figure 8:
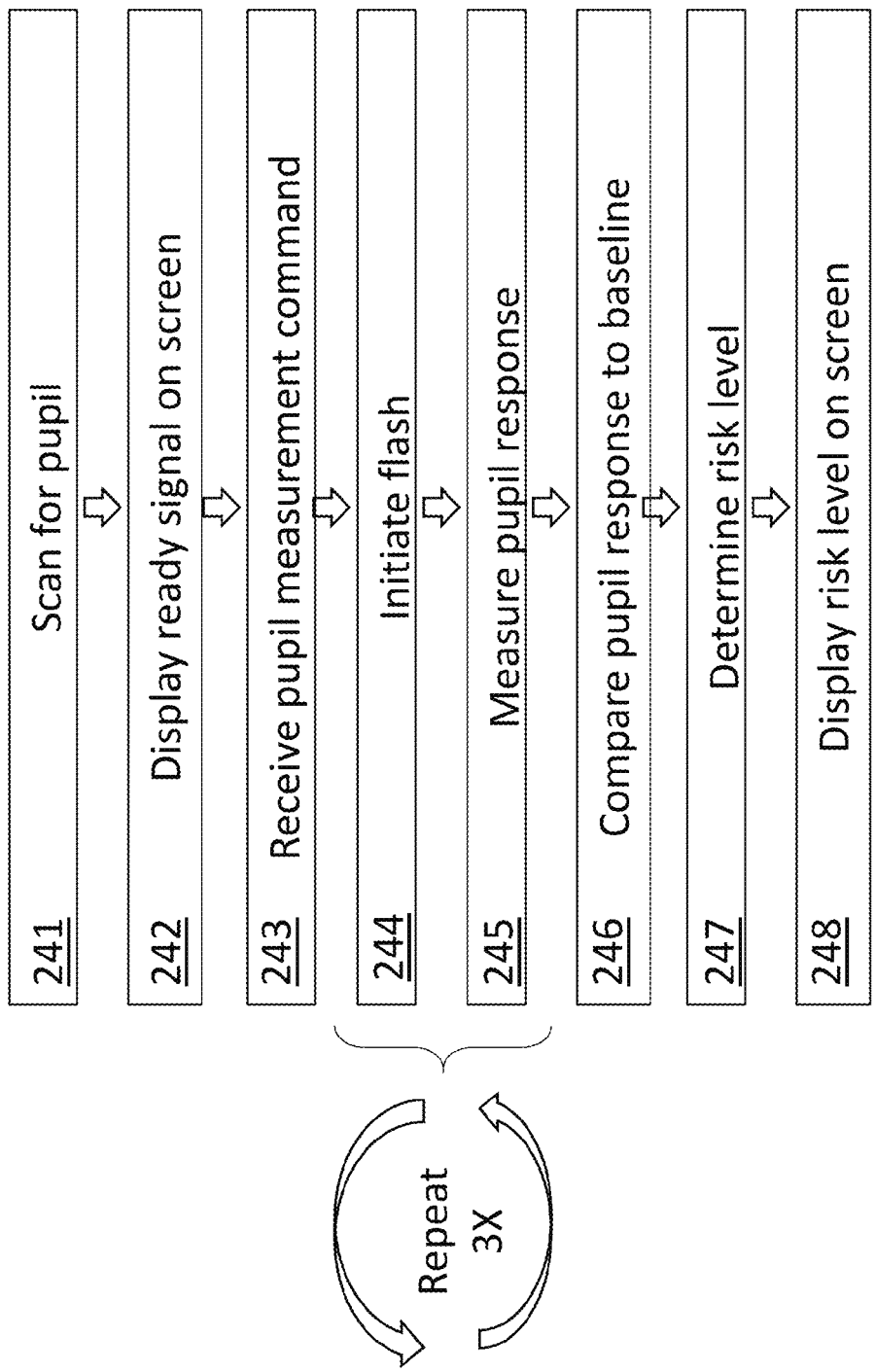
FIG. 8 is a flow chart diagram illustrating one embodiment of a process for measuring pupil response.
Figure 9:
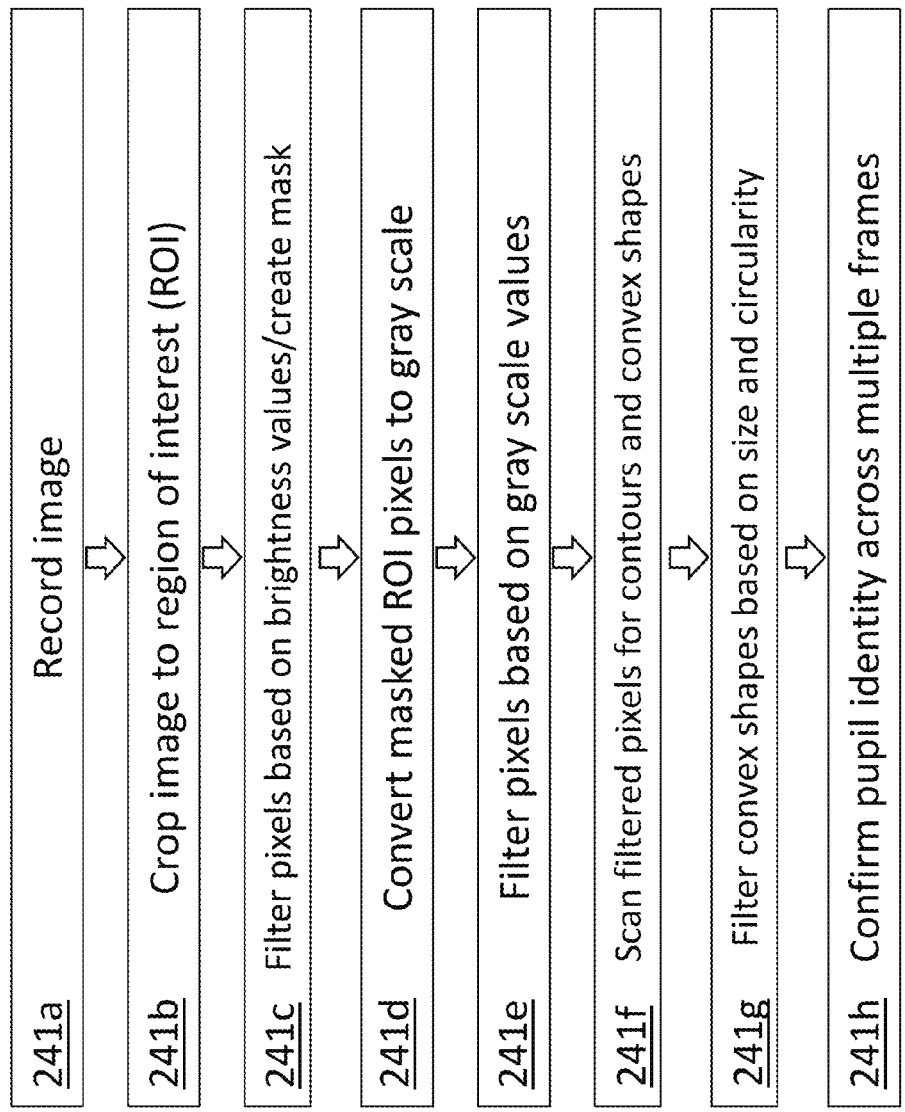
FIG. 9 is a flow chart diagram illustrating one embodiment of a process for scanning an image for a pupil.

FIGS. 7-9 depict one embodiment of a process for detecting brain trauma through measuring pupillary response. As will be apparent below, not all the elements discussed in connection with FIGS. 7-9 are depicted in FIGS. 7-9. Accordingly, reference will be made to other figures, such as FIGS. 4-6, for depictions of some of the elements discussed in the corresponding paragraphs. As shown in FIG. 7, a process 200 for detecting brain trauma may include the steps of directing 210 patient (6, FIG. 6) to an appropriately-lit area, opening 220 a pupil measurement application running on brain trauma detection device 100 (shown in FIGS. 4-6), orienting 230 digital camera 110 of device 100 to view patient's pupil, initiating 240 a pupil response measurement, retrieving 250 a pupil response risk level, and administering 260 an appropriate medical response. In the paragraphs that follow, each one of steps 210-260 is discussed in more detail.

The step of directing 210 patient 6 to an adequately-lit area may include directing patient 6 out of a shaded area and into an area with ambient light from, for example, the sun 55. Light allows camera 110 of device to capture distinctions between features of patient's eye 10, such as pupil 18. In some embodiments, step 210 may comprise a step of providing shade to eye 10 to filter or limit the amount of ambient light reaching patient's eye 10 to ensure that patient's eye 10 is not overly constricted before initiating flash 50.

Opening 220 pupil measurement application may include executing an application, such as a smartphone app, configured to control or manipulate various components of device 100, such as computer processor 140, computer memory 130, digital camera 110, lighting element 112, such as a flash, battery 160, and screen 40. To orient or fix camera on patient's pupil 18 (step 230), user 4 may move and orient camera 110 and/or device 100 until patient's pupil falls within a region of interest ("ROI") demarcated by one or more boundary lines or curves (e.g., 32, FIGS. 4A, 4B). In some embodiments, boundary lines 32 may define a rectangle extending across about 30% of the width of screen 40, and 30% of the length of screen 40.

With pupil measurement application open and camera 110 fixed on patient's pupil 18, user 4 can initiate pupil response step 240. User 4 may initiate the pupil response measurement by clicking a button or selecting an option on screen 40 (FIGS. 4A, 4B). Step 240 may comprise separate steps 241-248, as depicted in FIG. 8, and discussed in more detail below. Device 100 running the pupil measurement application carries out steps 241-248, and displays patient's risk level on screen 40. User 4 then retrieves the risk level 250 by looking at the results shown on screen 40, which may show low risk, medium risk, or high risk (or any other indicator of risk, e.g., numeric, etc.) and administers an appropriate medical response 260 corresponding with patient's risk level.

For example, if patient's risk level is high risk, user 4 may contact emergency response, medical personnel, or may take patient 6 to a hospital. If patient's risk level is medium risk, user 4 may administer first aid to patient 6, or may contact a doctor for instructions on the appropriate medical care for patient 6. For low risk, user 4 may administer no medical response, or may wait a period of time before measuring patient's pupil response again. In some embodiments, device 100 may display on screen 40 the appropriate protocol depending on the level of risk of brain trauma to patient 6, such as methods of treatment.

As mentioned earlier, pupil response step 240 may comprise several separate steps, such as steps 241-248, as depicted in FIG. 8. While the steps 210-260 shown in FIG. 7 can be initiated or carried out by user 4, steps 241-248 may be initiated by user 4, but carried out by device 100 running the pupil measurement application. Once user 4 has opened the application and directed camera 110 to scan patient's eye 10, device 100 may employ camera 110 to scan for patient's pupil 18. Step 241 of scanning for patient's pupil 18 may comprise several individual steps, or sub-steps, such as steps 241a-241h illustrated in FIG. 9.

Once device 100 scans and locates patient's pupil 10, device 100 may then indicate 242 to user 4 on screen 40 that application is ready to measure patient's pupil response. User 4 then may input a measurement command by, for example, selecting an option on screen 40, which input is received by device 100. Once measurement command 243 is received by device 100, device 100 may then initiate 244 flash, which uses light element 112 to propagate a flash of light 50 onto patient's pupil 18. When pupil 18 receives flash of light 50, pupil 18 may constrict and/or dilate in response. As explained above, patient 6 may have a baseline pupil response when patient 6 has suffered no trauma. The baseline pupil response may be to constrict, at a certain rate (e.g., 32, FIG. 2), when pupil 18 receives the flash, and then to dilate (or "redilate") at a certain rate (e.g., 34, FIG. 2) to return to the initial pupil size. When patient 6 has suffered brain trauma, however, pupil response may change, for example, by changing the rate of constriction 32 and/or dilation 34, or by changing the latency of pupil 18 responding to flash 50.

Device 100 may begin measuring pupil 18 before, during, and/or after flash 50. To measure pupil response, device 100 may record several successive images (e.g., 60, FIGS. 4A, 4B) of pupil 18 responding to flash 50, and determine the relative change in pupil's size between each successive image. Because each of the successive images is taken at known intervals of time (for example, 30 frames per second), the application can determine the relative change in size between each image, and determine the pupil's relative change in size over time.

After measuring the pupil response through a full cycle of constriction and dilation, device 100 may repeat flash step 244 and measurement step 245 an additional two times to compare patient's pupil response to a baseline pupil response. Device 100 may use all three measurements by, for example, averaging the difference of each measurement cycle from the baseline response. In some embodiments, device 100 may compare each measured pupil response to a baseline response, and average the deviations. In other embodiments, device 100 may average the three pupil response measurements, and compare the averaged measured pupil responses to the baseline pupil response. The baseline pupil response may be specific to patient 6, or a general baseline used for all patients. For example, in one embodiment, device 100 may measure patient's baseline pupil response when patient 6 has experienced no recent brain trauma event, and may save the baseline for future comparison. In other embodiments, pupil measurement application may include a general baseline pupil response applicable to most or all patients.

Once device 100 has compared measured pupil response to the baseline pupil response, the application can determine a risk level of brain trauma or other conditions based on the deviation of measured pupil response to the baseline pupil response. A high deviation may indicate a high risk, a medium deviation may indicate a medium risk, and a small or no deviation may indicate a low risk. Once device 100 has determined a risk level, device 100 may display risk level on screen 40. As explained earlier with respect to FIG. 7, user may then administer an appropriate medical response based on the risk level displayed by application to user.

As depicted in FIG. 9, pupil scanning step 241 may comprise several independent steps or sub-steps 241a-241h.

In some embodiments, steps 241a-241h may run several times, or may loop until a command is received or a particular result is recorded. With pupil measurement application initiated and camera 110 oriented to show patent's pupil 18 within a region of interest (ROI), which is indicated on screen 40 by boundary lines or curves, device 100 may scan 241 for pupil.

To scan for pupil, device directs 241a camera 110 to record an image 60, and crops 241b image 60 to ROI, effectively discarding pixels that fall outside the ROI. An example of an ROI is shown in FIGS. 4A and 4B, as defined by boundary lines 32. Next, device 100 filters 241c pixels of image 60 based on color and brightness values. For example, device 100 may use HSV (hue, saturation, value) values, or LAB values ("L" for lightness, and "a-b" for color-opponent values) to determine thresholds for pixel filtering. For example, if using HSV format, device 100 may filter out pixels having a "V" value (which represents the brightness) of greater than 60. However, in some embodiments, device 100 may use LAB values to filter pixels. In the LAB format, the "L" value denotes the lightness or brightness of the pixel color value. Because pupil may be the darkest feature of patient's eye, the application may filter out, or discard, pixels having an L value greater than 50, thereby leaving only the pixels that are relatively darker and more likely to include pupil 18.

In some embodiments, device 100 may then duplicate the original ROI of image 60, but discard or ignore pixels filtered out during step 241c. In other words, device 100 creates a "mask" that includes pixels not filtered out during step 241c. Device 100 may then convert 241d the remaining pixels to a gray scale, and filter 241e the converted gray scale pixels based on the brightness or intensity values. For example, application may filter pixels having an L value higher than 45. Pixels remaining after step 241e may comprise parts of image 60 including pupil 18, and other pixels that include other parts of patient's eye 10, such as iris 16. In other words, pupil boundary 24 FIGS. 4A, 4B), may be found within the remaining pixels after step 241e.

To find pupil boundary 24, device 100 scans remaining pixels for contours defined by incremental gradients in gray scale values of pixels, and constructs shapes based on, or defined by, the contours (step 241f). Device 100 then filters 241g shapes based on size and circularity values. For example, a circle may have a circularity value at or near 1.0, while an elongated ellipse may have a circularity value of around 0.25. Because the shape of a human pupil, such as pupil 18, is circular, device 100 may filter out or ignore shapes with circularity values that are not at or around 1. Furthermore, device 100 may filter out or ignore shapes that fall outside of a certain size threshold based on the amount of pixels enclosed by the shapes. For example, although some shapes identified by application fall within the circularity limits, such shapes may comprise smaller features in eye 10 or image 60.

Steps 241a-241g may be repeated several times, or in a loop to continue to identify pupil 18 as camera 110 moves relative to pupil 18, and pupil 18 moves around the field of view of camera 110. Once device 100 has identified a shape that meets the size and circularity requirements according to step 241g, device 100 may verify or confirm that the identified shape is a pupil 241h by repeating steps 241a-241g several times and verifying that the shape appears in each successive frame or iteration of steps 241a-241g. Due to small and brief variations in lighting or orientation of camera, some shapes may be identified by camera 110 that do not represent features of eye, and such shapes may be observed or identified by device 100 for only few frames or moments. Device 100 confirms that an identified shape is patient's pupil 18 by verifying continuity in the shape over several frames. In some embodiments, step 241h may take place over two or more seconds, with device 100 processing 20-40 frames each second.

Steps 241a-241h may loop or repeat in many successive frames, and may also be used in other steps of process 200—particularly in step 240. For example, device 100 may use some or all of steps 241a-241h to measure 245 pupil response. To measure pupil response, device 100 must locate pupil 18 in each frame, and measure pupil's relative change in size from one frame to the next. So that device 100 can measure relative changes in size, pupil 18 must be identified in each frame, and size of pupil 18 must be determined in each frame based on the number of pixels within pupil boundary 24. Thus, device 100 may repeat steps 241a-241h in the carrying out of step 245. Furthermore, step 245 also comprises steps of recording the relative change in pupil's size (e.g., in number of pixels, or the average diameter of the detected pupil).

As will be understood, this disclosure also contemplates other methods of detecting brain trauma that may comprise some of the steps described previously. For example, in one embodiment, a method for detecting brain trauma may include the steps of providing shade to patient's eye 10 and/or to digital camera 110, from overhead or ambient light 55 so as to control, or partially control, the effect of light stimulus 50 provided by brain trauma detection device 100 to patient's eye 10, or to control, or partially control, one or more aspects of the images recorded by brain trauma detection device 100. In some embodiments, digital camera 110 comprises an infrared camera sensor to locate and distinguish pupil 18 from other features of patient's eye 10. In some embodiments, camera 110 may be located on same side of device 100 as screen 40 (e.g., a "selfie camera") to enable patient 6 to self-administer the pupil measurement application. In still other embodiments, device 100 may operate to simultaneously measure pupil response of both of patient's pupils 18. In this embodiment, device 100 may be a smartphone, and user 4 and/or patient 6 may orient camera 110 of smartphone 100 in "landscape" mode or orientation to view both pupils 18.

As noted above, although the present disclosure refers to a "brain trauma" detection device 100, the present disclosure also contemplates the use of brain trauma detection device 100 to detect mental impairment, physical disability, or other brain-related conditions or characteristics. For example, in one embodiment, brain trauma detection device 100 can be used to detect a state of intoxication of patient 6. In another embodiment, brain trauma detection device 100 may be used to detect or diagnose autism.

For more information on systems and methods for detecting brain trauma, mental impairment, physical disability, or other brain dysfunction through tracking one or more ocular responses, the following publications may be illustrative of some aspects of the present disclosure, and are attached below: Angel N. Boez, et al., *Quantitative Pupillometry: Normative Data in Healthy Pediatric Volunteers*, 103 J Neruosurg. (6 Suppl) 496-500 (2005); Jose E Capo-Aponte et al., *Pupillary Light Reflex as an Objective Biomarker for Early Identification of Blast-Induced mTBI*, 2013 J Spine S4, available at www.readcube.com/articles/10.4172/2165-7939.s4-004; William R. Taylor et al., *Quantitative Pupillometry, a New Technology: Normative Data and Preliminary Observations in Patients with Acute Head Injury*, 98 J Neurosurg. 205-213 (2003); Mechal Ciesla, Przemyslaw Koziol, *Eye Pupil Location Using Webcam*, available at https://arxiv.org/ftp/arxiv/papers/1202/1202.6517.pdf; Cihan Topal, Cuneyt Akinlar, *An Adaptive Algorithm for Precise Pupil Boundary Detection Using the Entropy of Contour Gradients*, available at https://ceng.anadolu.edu.tr/cv/eyetracking/download/PupilDetection.pdf.

The term "a" or "an" as used in the present disclosure means one, but not limited to one. For example, if the present disclosure describes a brain trauma detection device as comprising "a digital camera," the disclosure therefore contemplates a brain trauma detection device comprising one or more digital cameras. "Coupled" or "coupled to" may refer to a relationship between one or more components which are associated or in communication with one another, but not necessarily in direct contact with, or directly attached to, one another. Thus, two components may be described as "coupled to" one another although there are intermediate components between the two components.

The invention claimed is:

1. A method for determining risk of brain trauma, comprising
   providing a pupillometry device, the pupillometry device including:
      a digital camera;
      a light element;
      a user interface;
      a computer processor; and
      computer memory;
   orienting a patient's eye to receive ambient light, the patient's eye including a pupil;
   orienting the digital camera to view the patient's pupil;
   energizing the light element to emit a flash of light to the patient's pupil;
   capturing a series of images of the patient's pupil;
   determining the location and relative size of the patient's pupil in each image;
   determining, from the series of images and the relative size of the patient's pupil in each image, one or more rates of change of the size of the patient's pupil;
   comparing the rates of change of the size of the patient's pupil to one or more baseline rates of change;
   determining a risk level of brain trauma to the patient based on the deviation of the rates of change of the size of the patient's pupil from the one or more baseline rates of change; and
   indicating to the patient the risk level of brain trauma.

2. The method of claim 1, wherein the pupillometry device comprises a smartphone.

3. The method of claim 1, wherein the steps of
   energizing the light element,
   capturing a series of images of the patient's pupil,
   determining the location and size of the patient's pupil, and
   determining the rates of change in size of the patient's pupil,
   are repeated two additional times.

4. The method of claim 1, wherein the step of orienting the digital camera to view the patient's pupil includes orienting the digital camera such that the patient's pupil falls within a region of interest, the region of interest defining a portion of a field of view of the digital camera.

5. The method of claim 4, wherein the step of orienting the digital camera to view the patient's pupil further includes:
   capturing an image;
   scanning the image for the patient's pupil; and notifying the patient that the patient's pupil has been detected.

6. The method of claim 5, wherein the step of scanning the image for the patient's pupil includes:

filtering pixels of the captured image based on one or more pixel values;

identifying shapes defined by contours in the gradient of the remaining pixels;

filtering shapes based on circularity and size threshold values; and verifying pupil detection by tracking the remaining shapes in a plurality of successive images.

7. The method of claim 4, wherein the region of interest comprises a rectangle spanning across less than 10% of the field of view of the digital camera.

8. The method of claim 1, wherein the step of determining the location and size of the patient's pupil includes:

filtering pixels of a captured image based on one or more pixel values;

identifying shapes defined by contours in the gradient of the remaining pixels;

filtering shapes based on circularity and size threshold values; and verifying pupil detection by tracking the remaining shapes in a plurality of successive images.

9. The method of claim 1, wherein the digital camera comprises an infrared digital camera.

10. The method of claim 1, wherein the user interface is a touch screen, and the digital camera is on the same side of the pupillometry device as the touch screen, such that a patient can orient the digital camera to view the patient's pupil while simultaneously viewing the screen.

11. The method of claim 1, wherein the pupillometry device further comprises a wireless receiver and a wireless transmitter configured to transmit data to a wireless communication hub.

* * * * *